US006652516B1

United States Patent
Gough

(10) Patent No.: US 6,652,516 B1
(45) Date of Patent: *Nov. 25, 2003

(54) CELL NECROSIS APPARATUS

(75) Inventor: Edward J. Gough, Menlo Park, CA (US)

(73) Assignee: Rita Medical Systems, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/443,946

(22) Filed: Nov. 19, 1999

Related U.S. Application Data

(63) Continuation of application No. 09/028,436, filed on Feb. 24, 1998, now Pat. No. 6,080,150, and a continuation-in-part of application No. 09/020,182, filed on Feb. 6, 1998, now abandoned, which is a continuation-in-part of application No. 08/963,239, filed on Nov. 3, 1997, which is a continuation-in-part of application No. 08/605,323, filed on Feb. 14, 1996, now Pat. No. 5,728,143, which is a continuation-in-part of application No. 08/515,379, filed on Aug. 15, 1995, now Pat. No. 5,683,384.

(51) Int. Cl.$^7$ .............................................. A61B 18/18
(52) U.S. Cl. ......................................... 606/41; 607/101
(58) Field of Search ............................... 606/41, 42, 45, 606/49, 50; 607/100–102; 604/21, 22, 114

(56) References Cited

U.S. PATENT DOCUMENTS

| 5,370,675 A | * | 12/1994 | Edwards et al. | ............. 607/101 |
| 5,403,311 A | * | 4/1995 | Abele et al. | ................... 606/49 |
| 5,855,576 A | * | 1/1999 | LeVeen et al. | ................ 606/41 |
| 6,080,150 A | * | 6/2000 | Gough | ........................ 606/41 |

* cited by examiner

*Primary Examiner*—Michael Peffley
(74) *Attorney, Agent, or Firm*—Jacqueline F. Mahoney; Peter J. Dehlinger; Perkins Coie LLP

(57) ABSTRACT

A cell necrosis apparatus has a flexible introducer including a lumen and a distal end sufficiently sharp to penetrate tissue. An energy delivery device is positionable in the introducer as the introducer is advanced through tissue. The energy delivery device includes a first RF electrode with a tissue piercing distal portion and a second RF electrode with a tissue piercing distal portion. The first and second RF electrodes are deployable with curvature from the introducer at a selected tissue site in a lateral direction away from the periphery of the introducer.

30 Claims, 9 Drawing Sheets

FIG.—1

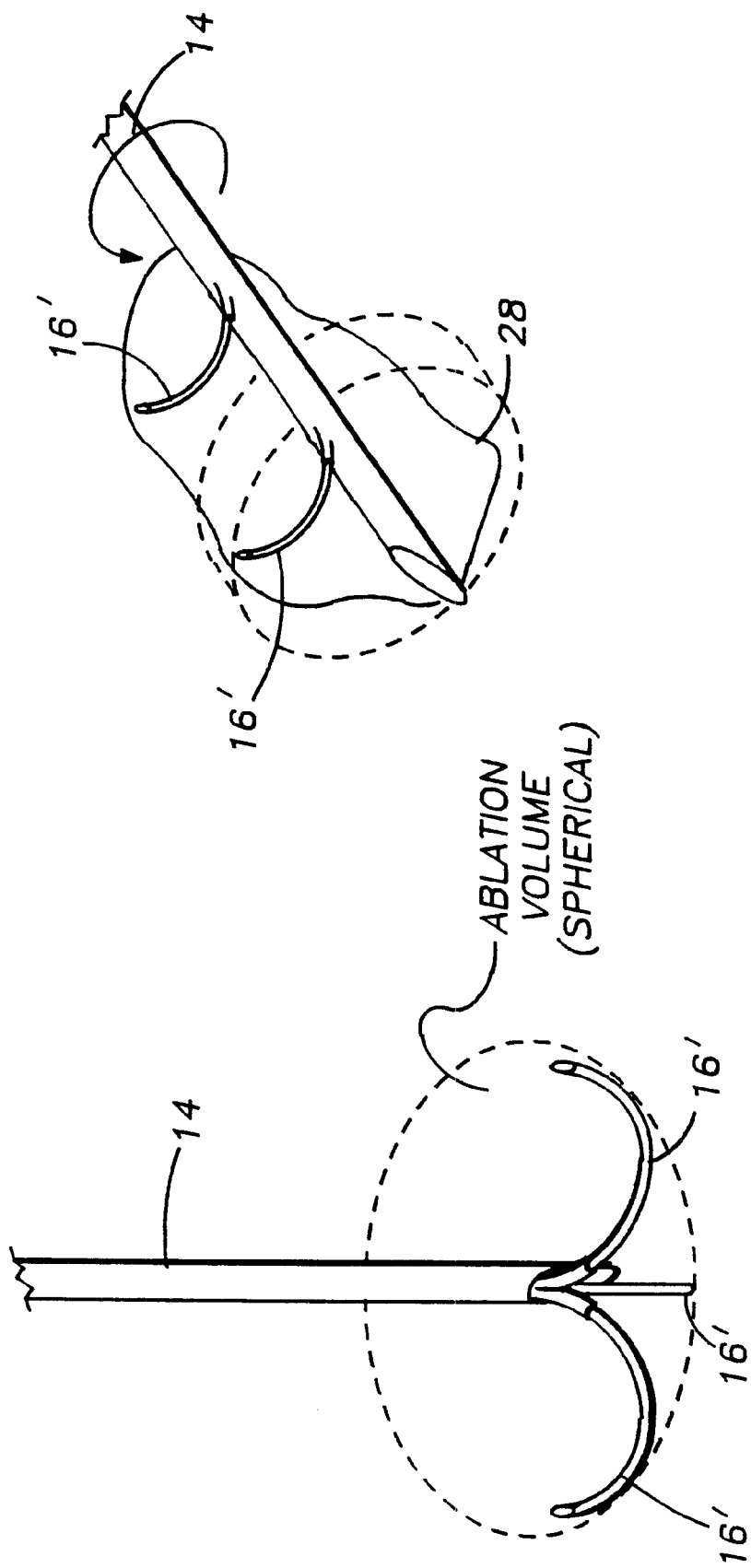

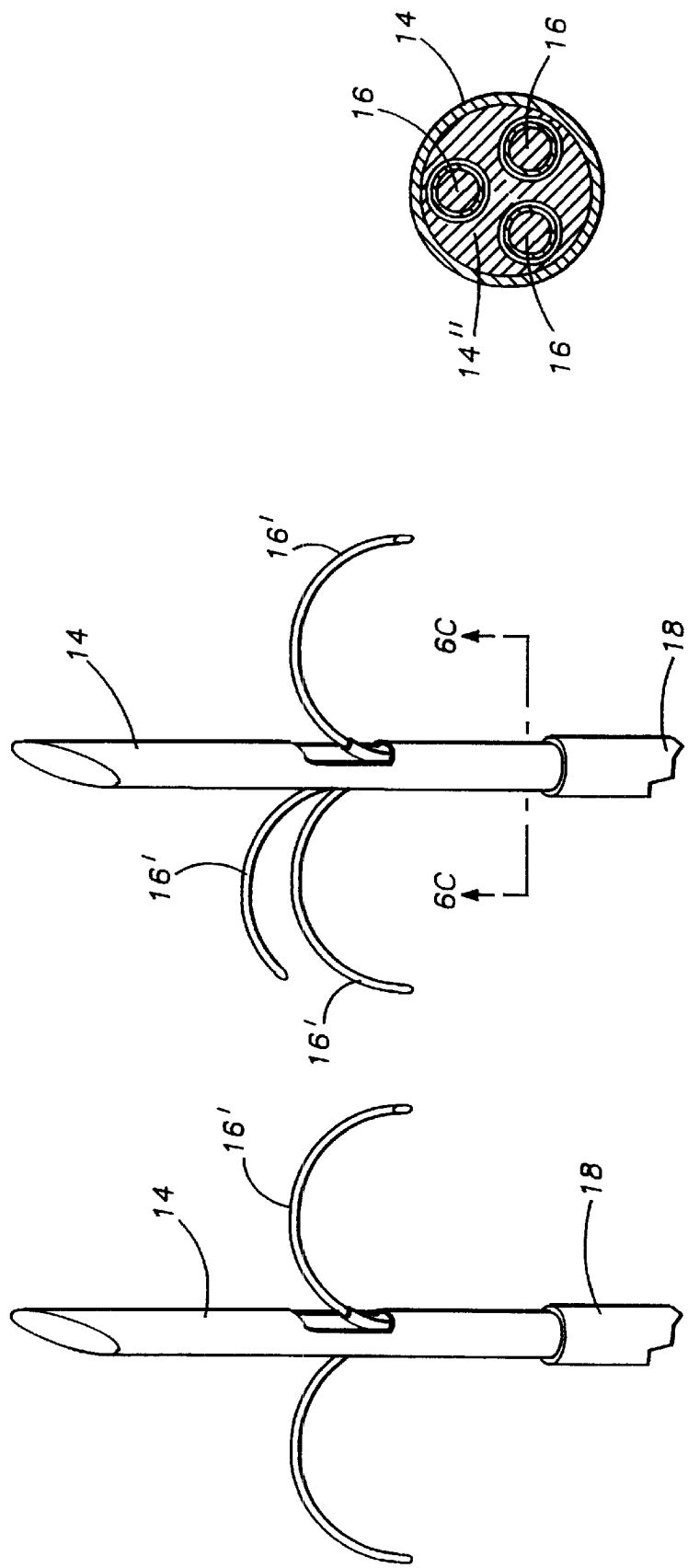

CELL NECROSIS APPARATUS

RELATIONSHIP TO COPENDING APPLICATIONS

This application is a Continuation of application Ser. No. 09/028,436, filed Feb. 24, 1998, now U.S. Pat. No. 6,080, 150, which is a continuation-in-part of application Ser. No. 09/020,182, filed Feb. 6, 1998 now abandoned, which is a continuation-in-part of application Ser. No. 08/963,239, filed Nov. 3, 1997, which is a continuation-in-part of application Ser. No. 08/605,323, filed Feb. 14, 1996, now U.S. Pat. No. 5,728,143, which is a continuation-in-part of application Ser. No. 08/515,379, filed Aug. 15, 1995, now U.S. Pat. No. 5,683,384, each of which is incorporated herein by reference in its entirety.

BACKGROUND OF THE INVENTION

1. Field of the Invention

This invention relates generally to a cell necrosis apparatus, and more particularly to a cell necrosis apparatus with a flexible introducer.

2. Description of the Related Art

Current open procedures for treatment of tumors are extremely disruptive and cause a great deal of damage to healthy tissue. During the surgical procedure, the physician must exercise care in not cutting the tumor in a manner that creates seeding of the tumor, resulting in metastasis. In recent years, development of products has been directed with an emphasis on minimizing the traumatic nature of traditional surgical procedures.

There has been a relatively significant amount of activity in the area of hyperthermia as a tool for treatment of tumors. It is known that elevating the temperature of tumors is helpful in the treatment and management of cancerous tissues. The mechanisms of selective cancer cell eradication by hyperthermia are not completely understood. However, four cellular effects of hyperthermia on cancerous tissue have been proposed, (i) changes in cell or nuclear membrane permeability or fluidity, (ii) cytoplasmic lysomal disintegration, causing release of digestive enzymes, (iii) protein thermal damage affecting cell respiration and the synthesis of DNA or RNA and (iv) potential excitation of immunologic systems. Treatment methods for applying heat to tumors include the use of direct contact radio-frequency (RF) applicators, microwave radiation, inductively coupled RF fields, ultrasound, and a variety of simple thermal conduction techniques.

Among the problems associated with all of these procedures is the requirement that highly localized heat be produced at depths of several centimeters beneath the surface of the skin.

Attempts to use interstitial local hyperthermia have not proven to be very successful. Results have often produced nonuniform temperatures throughout the tumor. It is believed that tumor mass reduction by hyperthermia is related to thermal dose. Thermal dose is the minimum effective temperature applied throughout the tumor mass for a defined period of time. Because blood flow is the major mechanism of heat loss for tumors being heated, and blood flow varies throughout the tumor, more even heating of tumor tissue is needed to ensure effective treatment.

The same is true for ablation of the tumor itself through the use of RF energy. Different methods have been utilized for the RF ablation of masses such as tumors. Instead of heating the tumor it is ablated through the application of energy. This process has been difficult to achieve due to a variety of factors including, (i) positioning of the RF ablation electrodes to effectively ablate all of the mass, (ii) introduction of the RF ablation electrodes to the tumor site and (iii) controlled delivery and monitoring of RF energy to achieve successful ablation without damage to non-tumor tissue.

Thus, non-invasive procedures for providing heat to internal tissue have had difficulties in achieving substantial specific and selective treatment.

Examples illustrating the use of electromagnetic energy to ablate tissue are disclosed in: U.S. Pat. Nos. 4,562,200; 4,411,266; 4,838,265; 5,403,311; 4,011,872; and 5,385,544.

There is a need for a cell necrosis apparatus with a flexible introducer. There is another need for a cell necrosis apparatus with an introducer that is flexible enough to come back upon itself. There is yet another need for a cell necrosis apparatus with an introducer that is advanceable through or around a selected target cell necrosis mass, and be flexibly positioned at any desired site in tissue.

SUMMARY OF THE INVENTION

Accordingly, an object of the invention is to provide a cell necrosis apparatus that provides tissue reduction at selected anatomical sites.

Another object of the invention is to provide a treatment apparatus to create cell necrosis.

Another object of the invention is to provide a cell necrosis apparatus with a flexible introducer.

Still another object of the invention is to provide a cell necrosis apparatus with an introducer that is flexible enough to come back upon itself.

A further object of the invention is to provide a cell necrosis apparatus with an introducer that is configured to be advanceable through or around a selected target cell necrosis mass, and be flexibly positioned at any desired site in tissue.

These and other objects of the invention are achieved in a cell necrosis apparatus with a flexible introducer including a lumen and a distal end sufficiently sharp to penetrate tissue. An energy delivery device is positionable in the introducer as the introducer is advanced through tissue. The energy delivery device includes a first RF electrode with a tissue piercing distal portion and a second RF electrode with a tissue piercing distal portion. The first and second RF electrodes are deployable with curvature from the introducer at a selected tissue site in a lateral direction away from the periphery of the introducer.

A further object of the invention is to provide a cell necrosis apparatus, with an introducer including a lumen and an energy delivery device including at least a first, a second and a third RF electrode. Each of the electrodes have a tissue piercing distal portion. The first, second and third RF electrodes are positionable in the introducer in a compacted state and deployable from the introducer with curvature in the deployed state. The first, second and third RF electrodes exhibit a changing direction of travel when advanced from the introducer to a selected tissue site. The first RF electrode may include a fluid delivery lumen and a fluid delivery port.

In another embodiment, the cell necrosis apparatus has a flexible introducer. The.energy delivery device includes a first RF electrode with a tissue piercing distal portion, a second RF electrode with a tissue piercing distal portion and a third RF electrode with a tissue piercing distal portion. The first, second and third RF electrodes are positionable in the introducer as the introducer is advanced through tissue and deployable with curvature in a radially divergent configuration when extended beyond the introducer.

BRIEF DESCRIPTION OF THE FIGURES

FIG. 4 is a perspective view illustrating three energy delivery devices creating a complete cell necrosis volume.

FIG. 5 is a perspective view illustrating the positioning of the cell necrosis apparatus in the center of a selected tissue mass, and the creation of a cylindrical ablation.

FIG. 6(a) is a perspective view of the cell necrosis of the present invention illustrating two energy delivery devices which provide a retaining and gripping function.

FIG. 6(b) is a perspective view of the cell necrosis apparatus of the present invention illustrating three secondary energy delivery devices which provide a retaining and gripping function.

FIG. 6(c) is a cross-sectional view of the apparatus of FIG. 6(b) taken along the lines 6(c)–6(c).

DETAILED DESCRIPTION

The present invention provides a cell necrosis apparatus with a flexible introducer. The apparatus is configured to be coupled to an energy source, a flexible introducer including a distal end, and a hollow lumen extending through the introducer and an energy delivery device with two or more energy delivery devices. The energy delivery devices can be initially positioned in the introducer lumen as the introducer is introduced through tissue or positioned in the introducer after or during its advancement through tissue. At a selected tissue site the energy delivery devices are deployable from the introducer lumen in a lateral direction relative to the longitudinal axis. Each of the deployed energy delivery devices has an electromagnetic energy delivery surface of sufficient size to, (i) create a volumetric cell necrosis between the deployed energy delivery devices, and (ii) create the volumetric cell necrosis without impeding out any of the deployed energy delivery devices when 5 to 200 watts of electromagnetic energy is delivered from the electromagnetic energy source to the cell necrosis apparatus.

At least one cable couples the cell necrosis apparatus to the electromagnetic energy source. For purposes of this specification the term "impeding out" means that a tissue area has become sufficiently desiccated or carbonized that the desiccated or carbonized tissue area has a resultant high electrical resistance that impairs the process of creating a coagulating lesion.

Figure 1:
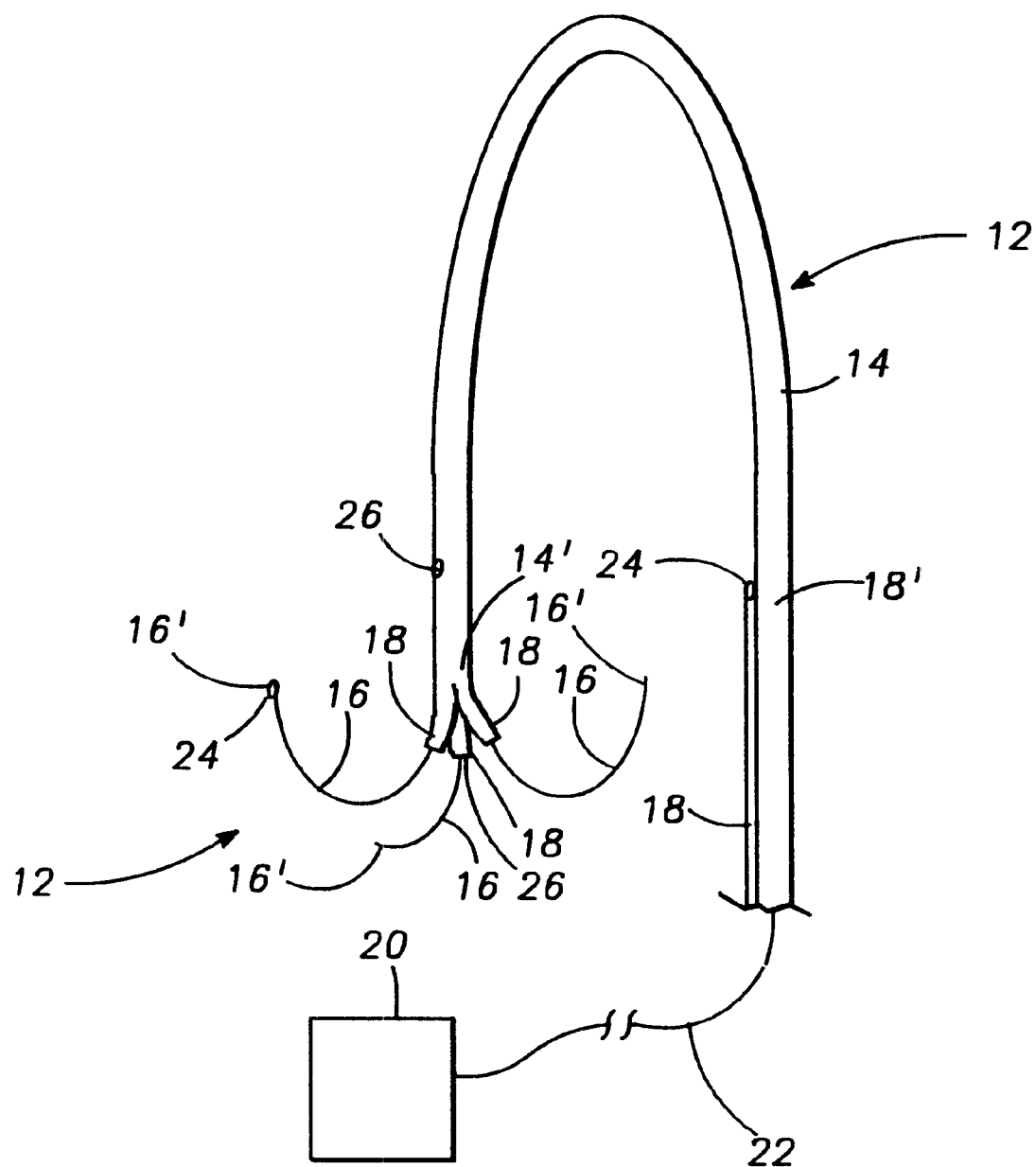
FIG. 1 is a perspective view of the cell necrosis apparatus of the present invention illustrating a flexible introducer and three laterally deployed energy delivery devices.

As shown in FIG. 1, cell necrosis apparatus 12 includes a flexible introducer 14, and one or more energy delivery devices 16, which are typically electrodes. Energy delivery devices 16 are initially positioned in an introducer lumen when introducer 14 is advanced through tissue. When introducer 14 reaches a selected tissue site, including but not limited to a solid lesion, energy delivery devices 16 are laterally deployed. Volumetric cell necrosis proceeds from the interior of the selected tissue mass in a direction towards a periphery of the selected tissue mass.

Each energy delivery device has a distal end 16' which distends away from and can surround a selected mass and may come back upon itself. Unless the distal ends 16' have insulation, then their entire length of extension is an electromagnetic energy delivery surface which delivers electromagnetic energy to the selected tissue mass. The length and size of each electromagnetic energy delivery surface can be variable. Lengths of energy delivery devices 16 can be adjustable. Introducer 14 can be moved up and down, rotated about its longitudinal axis, and moved back and forth, in order to define, along with sensors, the periphery or boundary of the selected tissue mass, including but not limited to a tumor. This provides a variety of different geometries, not always symmetrical, that can be ablated. Volumetric cell necrosis is defined as the creation of cell necrosis with a periphery formed between adjacent distal ends 16'. The volume of non-ablated tissue between adjacent distal ends 16' is minimized. A variety of different geometric cell necrosis zones are achieved including but not limited to spherical, semi-spherical, spheroid, triangular, semi-triangular, square, semi-square, rectangular, semi-rectangular, conical, semi-conical, quadrilateral, semi-quadrilateral, rhomboidal, semi-rhomboidal, trapezoidal, semi-trapezoidal, combinations of the preceding, geometries with non-planar sections or sides, free-form and the like.

In one embodiment, introducer 14 can have a sharpened distal end 14' to assist introduction through tissue. Each energy delivery device 16 has a distal end 16' that can be constructed to be less structurally rigid than introducer 14. Distal end 16' is the section of energy delivery device 16 that is advanced from the lumen introducer 14 and into the selected tissue mass.

Introducer 14 is sufficiently flexible to pierce tissue, and move in any direction through tissue to a selected tissue site. Introducer 14 is sufficiently flexible enough to come back upon itself. In one embodiment, introducer 14 is more flexible than energy delivery devices 16.

Energy delivery devices 16 can be made of a variety of conductive materials, both metallic and non-metallic. One suitable material is type 304 stainless steel of hypodermic quality. In some applications, all or a portion of secondary energy delivery device 16 can be made of a shaped memory metal, such as NiTi, commercially available from Raychem Corporation, Menlo Park, Calif.

Each of the energy delivery devices 16 can have different lengths. The lengths can be determined by the actual physical length of an energy delivery device 16, the length of an energy delivery device electromagnetic energy delivery surface, and the length of an energy delivery device 16 that is not covered by an insulator. Suitable lengths include but are not limited to 17.5 cm, 25.0 cm. and 30.0 cm. The actual length of an energy delivery device 16 depends on the location of the selected tissue mass to be ablated, its distance from the skin, its accessibility as well as whether or not the physician chooses a laparoscopic, percutaneous or other procedure.

An insulation sleeve 18 may be positioned around an exterior of introducer 14 and/or energy delivery devices 16. All or some of insulation sleeves 18 may be adjustably positioned so that the length of an energy delivery device electromagnetic energy delivery surface can be varied. Each insulation sleeve 18 surrounding an introducer 14 can include one or more apertures. This permits the introduction of a energy delivery device 16 through introducer 14 and insulation sleeve 18.

In one embodiment, insulation sleeve 18 comprises a polyamide material. A sensor 24 may be positioned on top of polyimide insulation sleeve 18. The polyamide insulation sleeve 18 is semi-rigid. Sensor 24 can lay down substantially along the entire length of polyamide insulation sleeve 18. Introducer 14 is made of a flexible material. Energy delivery devices 16 have distal ends 16' that are made of NiTi hypodermic tubing. A handle is included with markings to show the length of lateral deployment of energy delivery devices 16 from introducer 14. Fluid infusion is delivered through a Luer port at a side of the handle. Type-T thermocouples are positioned at distal ends 16'.

An electromagnetic energy source 20 is configured to be coupled to cell necrosis apparatus 12 with one or more cables 22. Electromagnetic energy source 20 can be an RF source, microwave source, short wave source, laser source and the like. Cell necrosis apparatus 12 can be comprised of energy delivery devices 16 that are RF electrodes, microwave antennas, as well as combinations thereof. Electromagnetic energy source 20 may be a combination RF/microwave box. Further a laser optical fiber, coupled to a laser source 20 can be introduced through one or both of introducer 14 or a energy delivery device 16. Introducer 14 and/or a secondary electrode 16 can be an arm for the purposes of introducing the optical fiber.

Energy delivery devices 16 are electromagnetically coupled to electromagnetic energy source 20. The coupling can be direct from electromagnetic energy source 20 to each energy delivery device 16, or indirect by using a collet, sleeve and the like which couples one or more energy delivery devices 16 to electromagnetic energy source 20. Electromagnetic energy can be delivered from one energy delivery device 16 to another.

One or more sensors 24 may be positioned on at least a portion of interior or exterior surfaces of introducer 14, energy delivery device 16 or insulation sleeve 18. Preferably sensors 24 are positioned at introducer distal end 14', energy delivery device distal end 16' and insulation sleeve distal end 18'. Sensors 24 permit accurate measurement of temperature at a tissue site in order to determine, (i) the extent of cell necrosis, (ii) the amount of cell necrosis, (iii) whether or not further cell necrosis is needed and (iv) the boundary or periphery of the ablated mass. Further, sensors 24 prevent non-targeted tissue from being destroyed or ablated.

Sensors 24 are of conventional design, including but not limited to thermistors, thermocouples, resistive wires, and the like. Suitable thermal sensors 24 include a T type thermocouple with copper constantene, J type, E type, K type, fiber optics, resistive wires, thermocouple IR detectors, and the like. It will be appreciated that sensors 24 need not be thermal sensors.

Sensors 24 measure temperature and/or impedance to permit monitoring and a desired level of cell necrosis to be achieved without destroying too much tissue. This reduces damage to tissue surrounding the targeted mass to be ablated. By monitoring the temperature at various points within the interior of the selected tissue mass, a determination of the selected tissue mass periphery can be made, as well as a determination of when cell necrosis is complete. If at any time sensor 24 determines that a desired cell necrosis temperature is exceeded, then an appropriate feedback signal is received at electromagnetic energy source 20 which then regulates the amount of electromagnetic energy delivered to energy delivery devices 16.

Thus the geometry of the ablated mass is selectable and controllable. Any number of different cell necrosis geometries can be achieved. Creation of different cell necrosis geometries is dependent on the length of electromagnetic energy cell necrosis delivery surfaces, the number of energy delivery devices, the size of the electromagnetic delivery surfaces, the amount of power delivered to the energy delivery devices, and the duration of time for power delivery to the energy delivery devices.

Energy delivery device distal ends 16' can be deployed from aperture 26 and distend away from introducer 14 in any number of different configurations, including but not limited to a "U" shape. Aperture 26 is at distal end 14' or formed in a side of an exterior of introducer 14.

In one embodiment, a method for creating a volumetric cell necrosis in a selected tissue mass provides cell necrosis apparatus 12 including introducer 14 with an introducer lumen, a plurality of energy delivery devices 16 deployable from the lumen, and an electromagnetic energy source 20 coupled to the plurality of energy delivery devices. Introducer 14 is inserted into the selected tissue mass with the plurality of energy delivery devices positioned in the introducer 14 lumen. The plurality of energy delivery devices 16 are advanced from the introducer lumen to distend away from introducer 14 to surround a selected mass before or after introducer 14 has pierced the selected cell necrosis site. 5 to 200 watts, preferably 5 to 100, and still more preferably 5 to 50 watts of electromagnetic energy is delivered from electromagnetic energy source 20 to the plurality of energy delivery devices 16 without impeding out an energy delivery device of the plurality of energy delivery devices. The volumetric cell necrosis is created between the plurality of energy delivery devices 16.

There is wide variation in the amount of deflection of energy delivery device 16. For example, energy delivery device 16 can be deflected a few degrees from the longitudinal axis of introducer 14, or energy delivery devices 16 can be deflected in any number of geometric configurations, including but not limited to a "J" hook. Further, energy delivery devices 16 are capable of being introduced from introducer 14 a few millimeters from introducer 14, or a much larger distance. In one embodiment, a distal portion of introducer 14 can also be an electromagnetic energy delivery surface.

Figure 2:
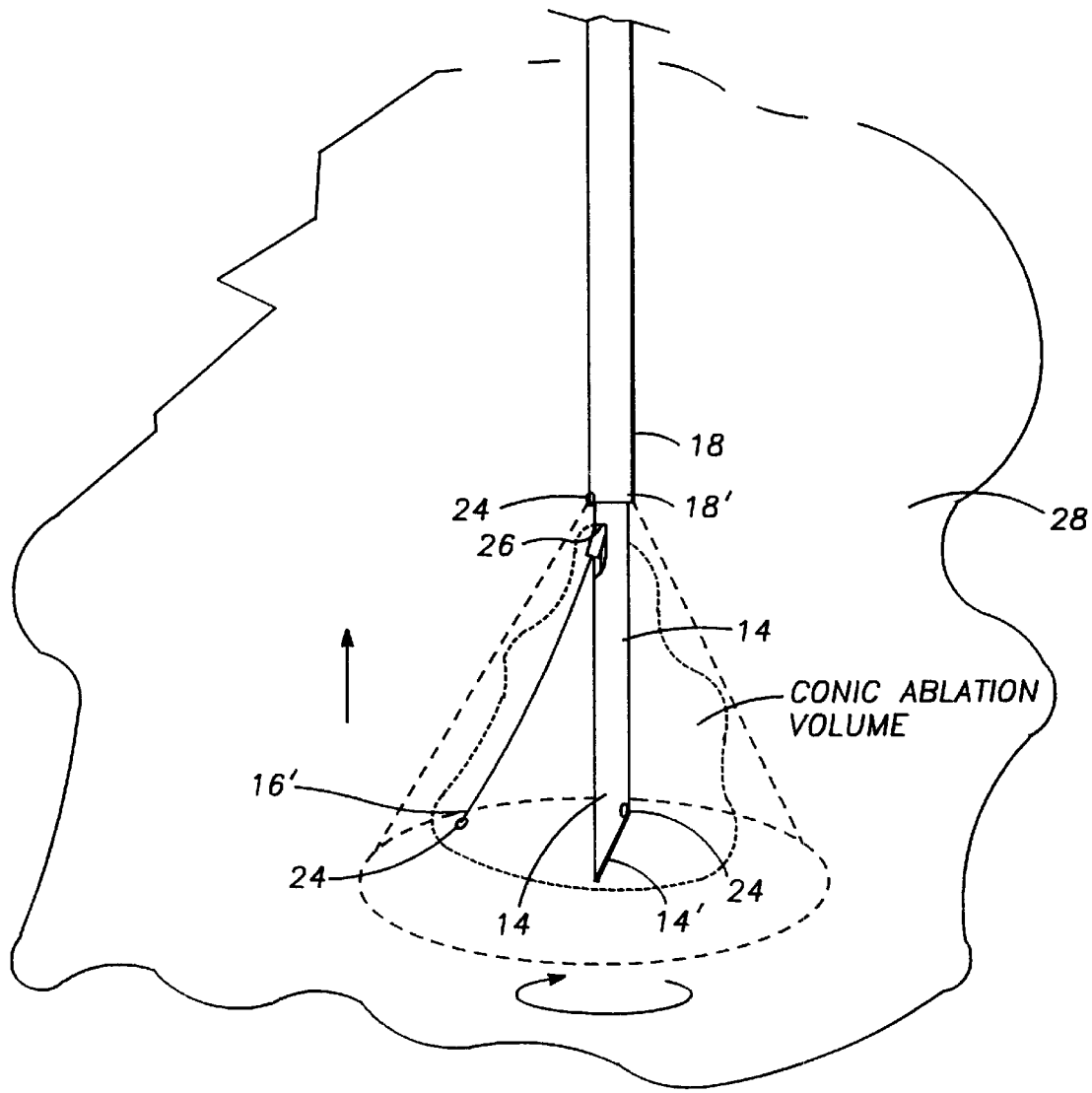
FIG. 2 is a perspective view of a conic geometric ablation achieved with the apparatus of FIG. 1.

As illustrated in FIG. 2, introducer 14 is introduced into a selected tissue mass 28. Three or more energy delivery devices 16 are positioned within an introducer lumen as introducer 14 is introduced into and through the selected tissue mass. In various embodiments, 3, 4, 5, or 6 energy delivery devices 16 are introduced laterally through introducer 14. Subsequently, energy delivery device distal end 16' is advanced out of aperture 26 into selected tissue mass 28. Insulation sleeves 18 are adjusted for energy delivery devices 16. RF, microwave, short wave and the like energy is delivery to energy delivery device 16 in a monopolar mode (RF), or alternatively, cell necrosis apparatus 12 can be operated in a bipolar mode (RF). Cell necrosis apparatus 12 can be switched between monopolar and bipolar operation and may have multiplexing capability between different energy delivery devices 16. Energy delivery device distal ends 16' is retracted back into introducer 14, and introducer is then rotated. Energy delivery device distal end 16' is then introduced into selected tissue mass 28. Energy delivery devices 16 may be introduced a short distance into selected tissue mass 28 to ablate a small area, e.g., 3 cm or less. It can then be advanced further into any number of times to create more cell necrosis zones. Again, energy delivery device distal end 16' is retracted back into introducer 14, and introducer 14 can be, (i) rotated again, (ii) moved along a longitudinal axis of selected tissue mass 28 to begin another series of cell necrosis zones with energy delivery device distal ends 16' being introduced and retracted in and out of introducer 14, or (iii) removed from selected tissue mass 28. A number of parameters permit cell necrosis of selected tissue masses 28 of different sign and shapes including a series of cell necrosis zones having energy delivery devices 16 with variable length electromagnetic energy delivery surfaces and the use of one or more sensors 24.

Figure 3:
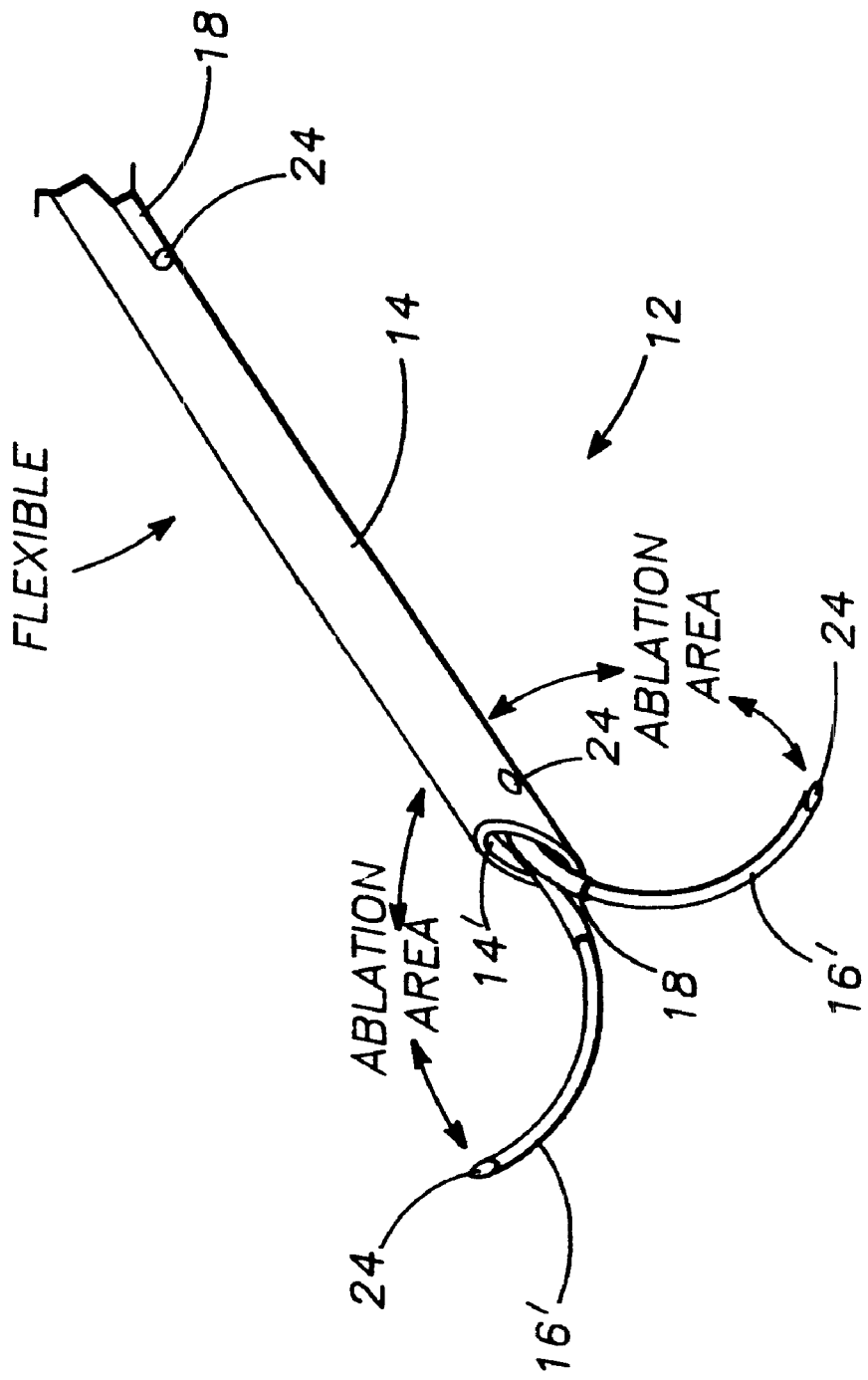
FIG. 3 is a perspective view of the cell necrosis apparatus of the present invention with two energy delivery devices.

In FIG. 3, two energy delivery devices 16 are each deployed out of distal end 14' and introduced into selected tissue mass 28. Energy delivery devices 16 form a plane and the area of cell necrosis extends between the electromagnetic energy delivery surfaces of energy delivery devices 16. Introducer 14 can be introduced in an adjacent relationship to selected tissue mass 28. This particular deployment is useful for small selected tissue masses 28, or where piercing selected tissue mass 28 is not desirable. Introducer 14 can be rotated, with energy delivery devices 16 retracted in the lumen of introducer 14, and another cell necrosis volume defined between the energy delivery devices 16 is created.

Further, introducer 14 can be withdrawn from its initial position adjacent to selected tissue mass 28, repositioned to another position adjacent to selected tissue mass 28, and energy delivery devices 16 deployed to begin another cell necrosis cycle. Any variety of different positions may be utilized to create a desired cell necrosis geometry for selected tissue mass of different geometries and sizes.

In FIG. 4, three energy delivery devices 16 are introduced into selected tissue mass 28. The effect is the creation of a substantially complete cell necrosis volume formed between energy delivery devices 16 with a minimal central core that is not ablated.

Referring now to FIG. 5, a center of selected tissue mass 28 is pierced by introducer 14, energy delivery devices 16 are laterally deployed and retracted, introducer 14 is rotated, energy delivery devices 16 are deployed and retracted, and so on until a cylindrical cell necrosis volume is achieved. Cell necrosis apparatus 12 can be operated in the bipolar mode between the two energy delivery devices 16, or between a energy delivery device 16 and introducer 14. Alternatively, cell necrosis apparatus 12 can be operated in a monopolar mode.

Energy delivery devices 16 can serve the additional function of anchoring cell necrosis apparatus 12 in a selected tissue mass, as illustrated in FIGS. 6(a) and 6(b). In FIG. 6(a) one or both energy delivery devices 16 are used to anchor and position introducer 14. Further, one or both energy delivery devices 16 are also used to ablate tissue. In FIG. 6(b), three energy delivery devices are deployed and anchor introducer 14.

FIG. 6(c) illustrates the infusion capability of cell necrosis apparatus 12. Three energy delivery devices 16 are positioned in a central lumen 14" of introducer 14. One or more of the energy delivery devices 16 can also include a central lumen coupled to an infusion source. Central lumen 14" is coupled to an infusion source and delivers a variety of infusion mediums to selected places both within and outside of the targeted cell necrosis mass. Suitable infusion mediums include but are not limited to, therapeutic agents, conductivity enhancement mediums, contrast agents or dyes, and the like. An example of a therapeutic agent is a chemotherapeutic agent.

Figure 8:
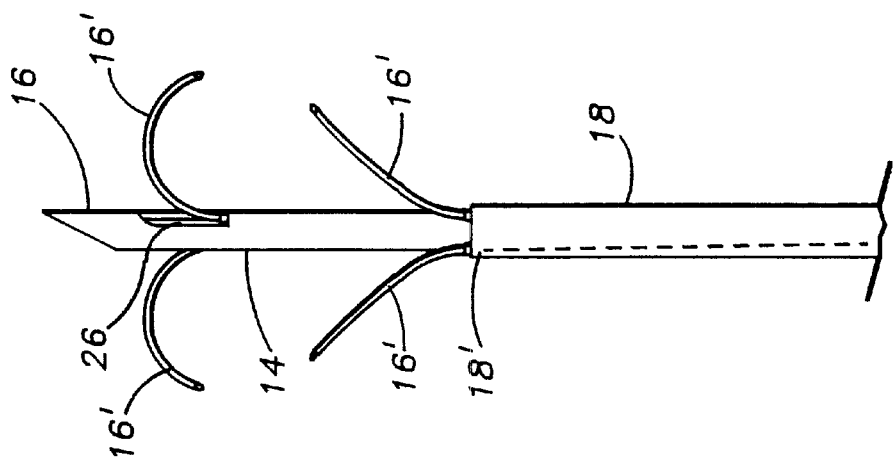
FIG. 8 is a perspective view of the cell necrosis apparatus of the present invention illustrating the deployment of two secondary energy delivery devices from the primary energy delivery device, and the deployment of three secondary energy delivery devices from the distal end of the insulation sleeve surrounding the primary energy delivery device.
Figure 7:
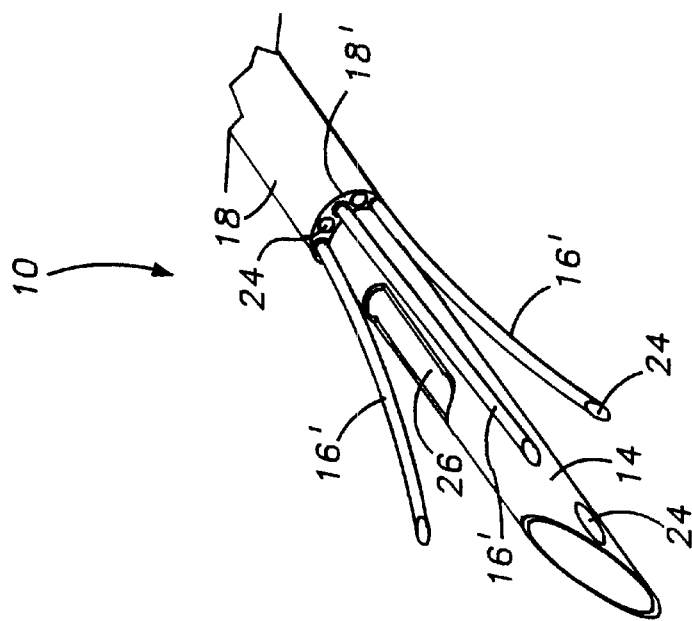
FIG. 7 is a perspective view of the cell necrosis apparatus of the present invention illustrating the deployment of three secondary energy delivery devices from a distal end of the insulation sleeve surrounding the primary energy delivery device.

As shown in FIG. 7, insulation sleeve 18 can include one or more lumens for receiving energy delivery devices 16 which are deployed out of an insulation sleeve distal end 18'. FIG. 8 illustrates two energy delivery devices 16 being introduced out of insulation sleeve distal end 18', and two energy delivery devices 16 introduced through apertures 26 formed in introducer 14. As illustrated, energy delivery devices 16 introduced through apertures 26 provide an anchoring function. FIG. 8 illustrates that energy delivery devices 16 can have a variety of different geometric configurations in cell necrosis apparatus 12.

A feedback control system 29 is connected to electromagnetic energy source 20, sensors 24 and energy delivery devices 16. Feedback control system 29 receives temperature or impedance data from sensors 24 and the amount of electromagnetic energy received by energy delivery devices 16 is modified from an initial setting of cell necrosis energy output, cell necrosis time, temperature, and current density (the "Four Parameters"). Feedback control system 29 can automatically change any of the Four Parameters. Feedback control system 29 can detect impedance or temperature and change any of the four parameters. Feedback control system 29 can include a multiplexer to multiplex different energy delivery devices, a temperature detection circuit that provides a control signal representative of temperature or impedance detected at one or more sensors 24. A microprocessor can be connected to the temperature control circuit.

Figure 11:
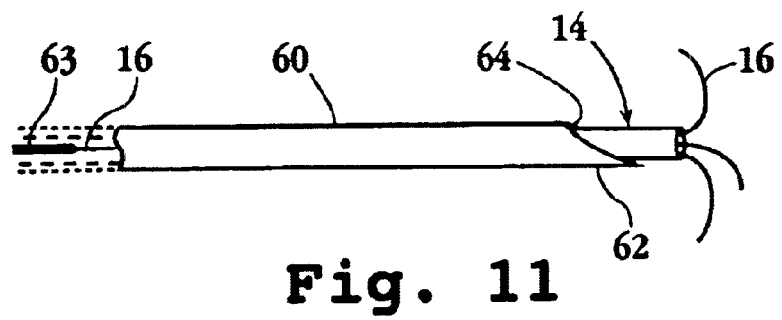
FIG. 11 is a perspective view of the cell necrosis apparatus of the present invention illustrating three energy delivery devices.

As illustrated in FIG. 11A, in another embodiment, an obturator 62 is located in the lumen 64 of the flexible introducer 14 as the introducer is advanced to the selected tissue site. At the selected tissue site, the obturator is removed. A rigid advancement member 63 coupled to the energy delivery devices 16 may be advanced through the introducer 14.

Figure 12A:
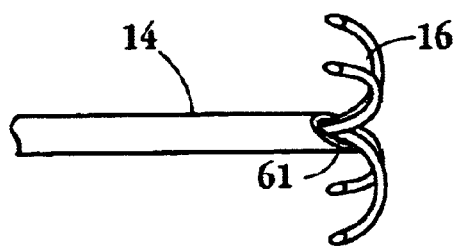
FIGS. 12A–12C are perspective views of the cell necrosis apparatus of the present invention illustrating four, five, and six energy delivery devices, respectively.
Figure 12B:
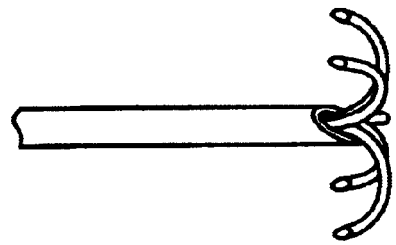
Figure 12C:
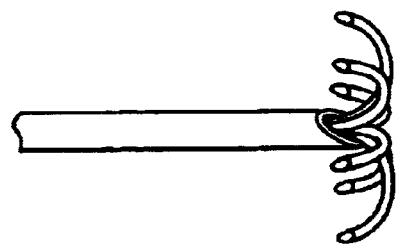

In FIGS. 12A–12C, four, five or six energy delivery devices 16 are deployed out of the introducer distal end 14'. The introducer 14 may have a fluid delivery port 61 coupled to the introducer lumen. One or all of the RF electrodes may include a fluid delivery lumen and a fluid delivery port 65.

The following discussion pertains particularly to the use of an RF energy source and RF electrodes but applies to other energy delivery devices and energy sources including but not limited to microwave, ultrasound, resistive heating, coherent and incoherent light, and the like.

Figure 9:
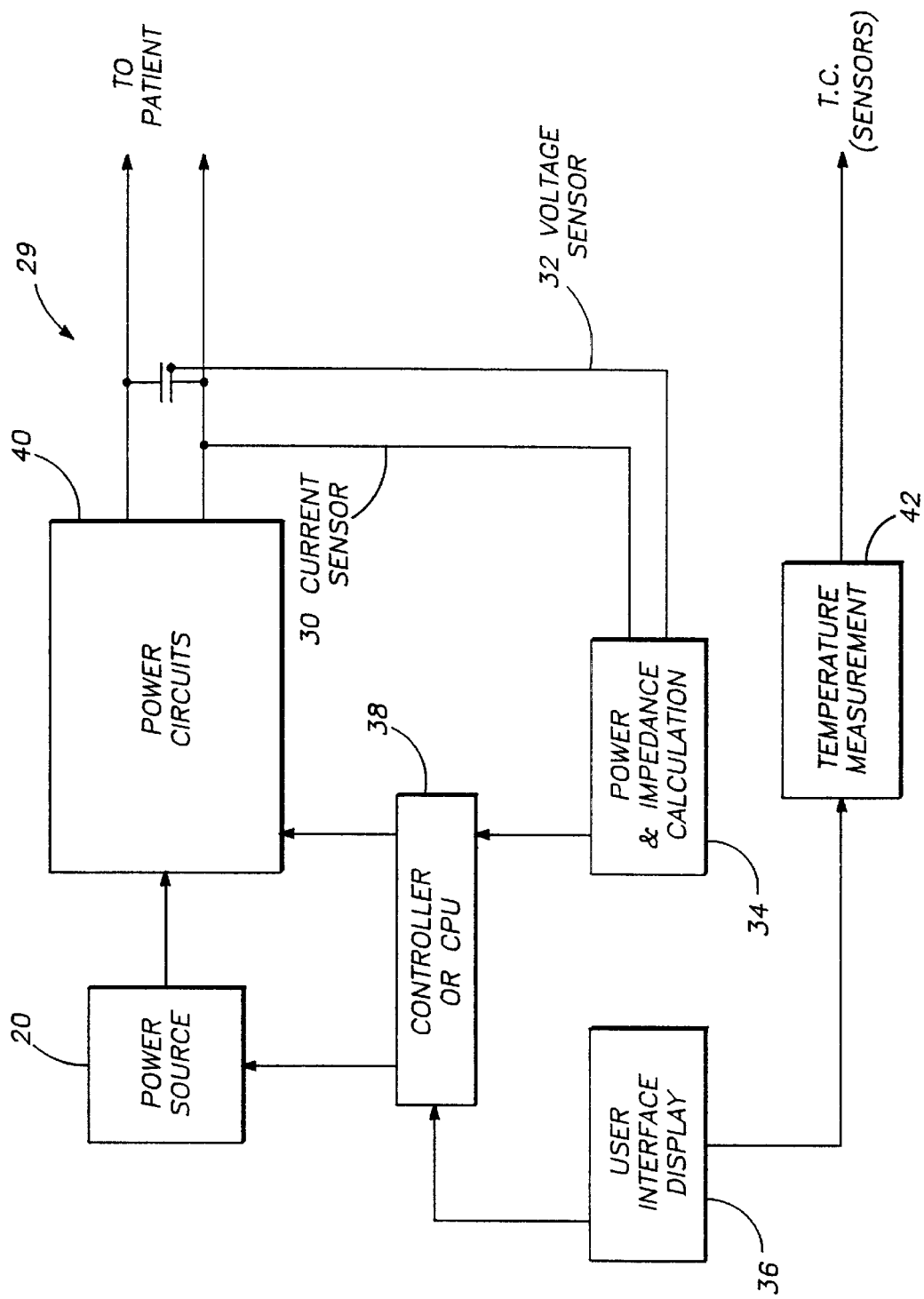
FIG. 9 is a block diagram illustrating the inclusion of a controller, electromagnetic energy source and other electronic components of the present invention.

Referring now to FIG. 9, all or portions of feedback control system 29 are illustrated. Current delivered through energy delivery devices 16 is measured by current sensor 30. Voltage is measured by voltage sensor 32. Impedance and power are then calculated at power and impedance calculation device 34. These values can then be displayed at user interface and display 36. Signals representative of power and impedance values are received by controller 38.

A control signal is generated by controller 38 that is proportional to the difference between an actual measured value, and a desired value. The control signal is used by power circuits 40 to adjust the power output in an appropriate amount in order to maintain the desired power delivered at energy delivery devices 16.

In a similar manner, temperatures detected at sensors 24 provide feedback for determining the extent of cell necrosis, and when a completed cell necrosis has reached the physical location of sensors 24. The actual temperatures are measured at temperature measurement device 42 and the temperatures are displayed at user interface and display 36. A control signal is generated by controller 38 that is proportional to the difference between an actual measured temperature, and a desired temperature. The control signal is used by power circuits 40 to adjust the power output in an appropriate amount in order to maintain the desired temperature delivered at the respective sensor 24. A multiplexer can be included to measure current, voltage and temperature, at the numerous sensors 24, and energy is delivered to energy delivery devices 16.

Controller 38 can be a digital or analog controller, or a computer with software. When controller 38 is a computer it can include a CPU coupled through a system bus. On this system can be a keyboard, a disk drive, or other non-volatile memory systems, a display, and other peripherals, as are known in the art. Also coupled to the bus are a program memory and a data memory.

User interface and display 36 includes operator controls and a display. Controller 38 can be coupled to imaging systems, including but not limited to ultrasound, CT scanners, X-ray, MRI, mammographic X-ray and the like. Further, direct visualization and tactile imaging can be utilized.

The output of current sensor 30 and voltage sensor 32 is used by controller 38 to maintain a selected power level at energy delivery devices 16. The amount of RF energy delivered controls the amount of power. A profile of power delivered can be incorporated in controller 38, and a preset amount of energy to be delivered can also be profiled.

Circuitry, software and feedback to controller 38 result in process control, and the maintenance of the selected power, and are used to change, (i) the selected power, including RF, microwave, laser and the like, (ii) the duty cycle (on-off and wattage), (iii) bipolar or monopolar energy delivery and (iv) infusion medium delivery, including flow rate and pressure. These process variables are controlled and varied, while maintaining the desired delivery of power independent of changes in voltage or current, based on temperatures monitored at sensors 24.

Figure 10:
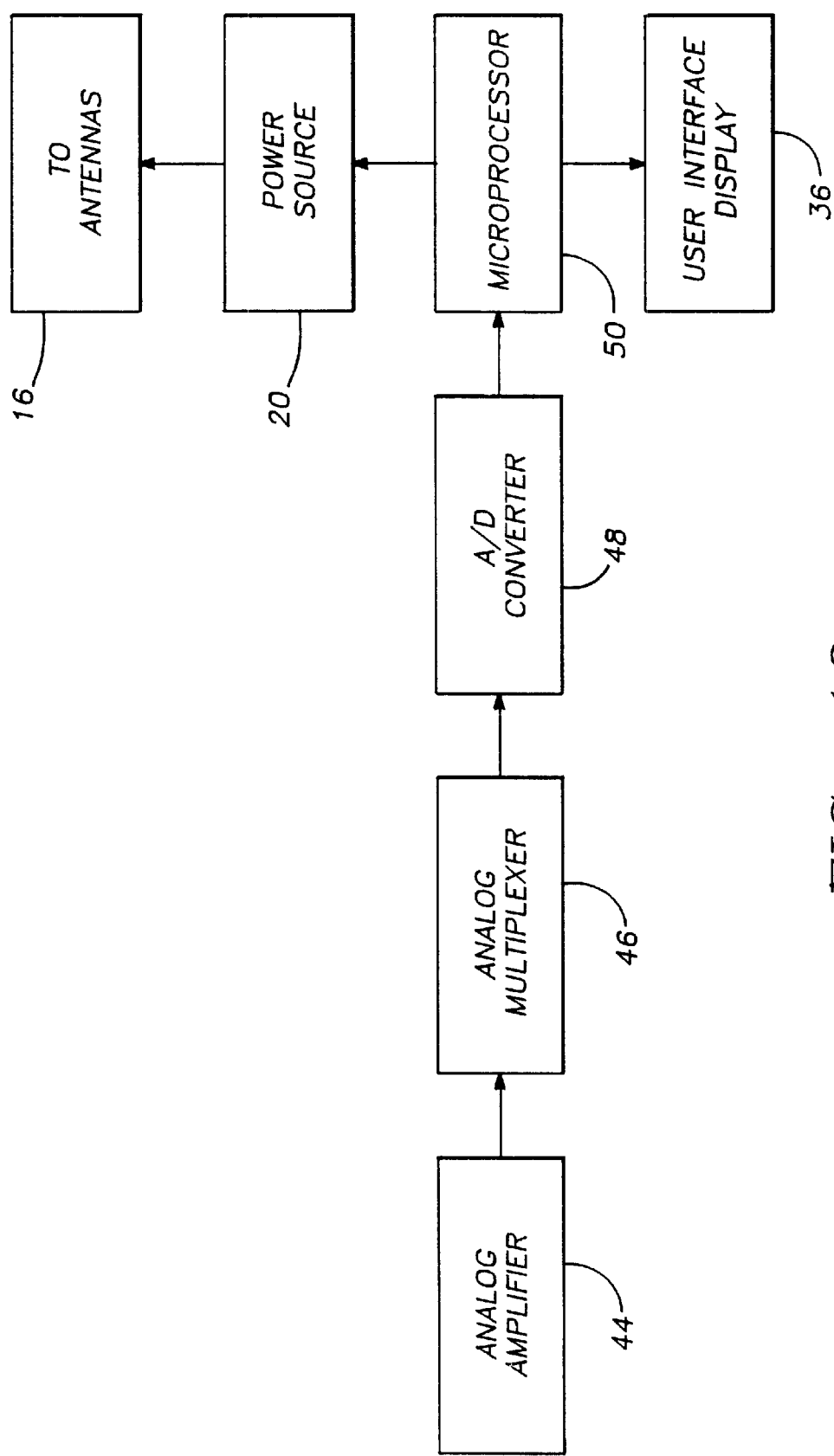
FIG. 10 is a block diagram illustrating an analog amplifier, analog multiplexer and microprocessor used with the present invention.

Referring now to FIG. 10, current sensor 30 and voltage sensor 32 are connected to the input of an analog amplifier 44. Analog amplifier 44 can be a conventional differential amplifier circuit for use with sensors 24. The output of analog amplifier 44 is sequentially connected by an analog multiplexer 46 to the input of A/D converter 48. The output of analog amplifier 44 is a voltage which represents the respective sensed temperatures. Digitized amplifier output voltages are supplied by A/D converter 48 to a microprocessor 50. Microprocessor 50 may be Model No. 68HCII available from Motorola. However, it will be appreciated that any suitable microprocessor or general purpose digital or analog computer can be used to calculate impedance or temperature.

Microprocessor 50 sequentially receives and stores digital representations of impedance and temperature. Each digital value received by microprocessor 50 corresponds to different temperatures and impedances.

Calculated power and impedance values can be indicated on user interface and display 36. Alternatively, or in addition to the numerical indication of power or impedance, calculated impedance and power values can be compared by microprocessor 50 with power and impedance limits. When the values exceed predetermined power or impedance values, a warning can be given on user interface and display 36, and additionally, the delivery of RF energy can be reduced, modified or interrupted. A control signal from microprocessor 50 can modify the power level supplied by electromagnetic energy source 20.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A cell necrosis apparatus, comprising:

an introducer including a lumen;

an energy delivery device including at least a first, a second and a third RF electrode each with a tissue piercing distal portion, the first, second and third RF electrodes being positionable in the introducer in a compacted state and preformed to assume a curved shape when deployed, the first, second and third RF electrodes exhibiting a changing direction of travel when advanced from the introducer to a selected tissue site, the first RF electrode including a fluid delivery lumen and a fluid delivery port.

2. The apparatus of claim 1, further comprising:

a rigid electrode advancement member coupled to the energy delivery device.

3. The apparatus of claim 1, further comprising:

an impedance measurement apparatus coupled to the energy delivery device.

4. The apparatus of claim 1, further comprising:

an insulator positioned in a surrounding relationship to at least a portion of the introducer.

5. The apparatus of claim 1, further comprising:

a sensor coupled to the first RF electrode.

6. The apparatus of claim 5, wherein the sensor is a thermal sensor.

7. The apparatus of claim 1, further comprising:

a sensor coupled to the introducer.

8. The apparatus of claim 7, further comprising:

a feedback control coupled to the sensor and to the first RF electrode.

9. The apparatus of claim 1, wherein the introducer includes a tissue penetrating distal end.

10. The apparatus of claim 1, wherein the first, second and third RF electrodes define an ablation volume in the deployed state at the selected tissue site.

11. The apparatus of claim 1, wherein the second RF electrode includes a fluid delivery lumen and a fluid delivery port.

12. The apparatus of claim 11, wherein the third RF electrode includes a fluid delivery lumen and a fluid delivery port.

13. The apparatus of claim 1, wherein the energy delivery device further includes a fourth RF electrode positionable in the introducer in a compacted state and deployable from the introducer with curvature in the deployed state, the fourth RF electrode exhibiting a changing direction of travel when advanced from the introducer to the selected tissue site.

14. The apparatus of claim 13, wherein the fourth RF electrode includes a fluid delivery lumen and a fluid delivery port.

15. The apparatus of claim 13, wherein the energy delivery device further includes a fifth RF electrode positionable in the introducer in a compacted state and deployable from the introducer with curvature in the deployed state, the fifth RF electrode exhibiting a changing direction of travel when advanced from the introducer to the selected tissue site.

16. The apparatus of claim 15, wherein the fifth RF electrode includes a fluid delivery lumen and a fluid delivery port.

17. The apparatus of claim 16, wherein the energy delivery device further includes a sixth RF electrode positionable in the introducer in a compacted state and deployable from the introducer with curvature in the deployed state, the sixth RF electrode exhibiting a changing direction of travel when advanced from the introducer to the selected tissue site.

18. The apparatus of claim 17, wherein the sixth RF electrode includes a fluid delivery lumen and a fluid delivery port.

19. The apparatus of claim 1, wherein a distal portion of the introducer includes a fluid delivery port coupled to the lumen of the introducer.

20. The apparatus of claim 19, wherein the first, second and third RF electrodes are advanceable from introducer.

21. A cell necrosis apparatus, comprising:

a flexible introducer having a lumen, and having a tissue piercing distal end; and an energy delivery device including at least a first RF electrode with a first tissue piercing distal portion and a second RF electrode with a second tissue piercing distal portion, the first and second RF electrodes being positionable in the introducer, and preformed to assume a curved shape when deployed, and exhibiting a changing direction of travel as the electrodes are advanced to a selected tissue site.

22. The apparatus of claim 21, further comprising:

a rigid electrode advancement member coupled to the energy delivery device.

23. The apparatus of claim 21, wherein the first and second RF electrodes exhibit at the selected tissue the first curved section, the second section and a linear section coupled to the first and second curved sections.

24. The apparatus of claim 21, further comprising:

an insulator positioned in a surrounding relationship to at least a portion of the introducer.

25. The apparatus of claim 21, further comprising:

a sensor coupled to the first RF electrode.

26. The apparatus of claim 25, wherein the sensor is a thermal sensor.

27. The apparatus of claim 21, further comprising:

a sensor coupled to the introducer.

28. The apparatus of claim 27, further comprising:

a feedback control coupled to the sensor and to the first RF electrode.

29. The apparatus of claim 21, further comprising:

an impedance measurement apparatus coupled to the energy delivery device.

30. The apparatus of claim 21, further comprising:

a second introducer positionable within the lumen of the flexible introducer as the flexible introducer is introduced through tissue, wherein said at least first and second electrodes are positionable in the second introducer.

* * * * *